United States Patent [19]

Bilbo

[11] Patent Number: 5,011,629

[45] Date of Patent: Apr. 30, 1991

[54] HYDROXYSTEARIC POLYESTERS OF GUERBET ALCOHOLS AS POLYCARBONATE LUBRICANTS

[76] Inventor: Raymond E. Bilbo, 1008 Olde Hinge Way, Sneville, Ga. 30278

[21] Appl. No.: 338,897

[22] Filed: Apr. 17, 1989

[51] Int. Cl.$^5$ .............................................. C11C 3/100
[52] U.S. Cl. .................................. 260/405; 524/306; 560/180; 560/198
[58] Field of Search ................ 560/180, 198; 260/405; 521/143; 524/306

[56] References Cited

U.S. PATENT DOCUMENTS 3,917,555 11/1975 Worscheck et al. ................ 524/314
4,157,990 6/1979 Lindner et al. ..................... 524/314

FOREIGN PATENT DOCUMENTS 0108739 8/1981 Japan ................................... 260/405

*Primary Examiner*—Jose G. Dees
*Assistant Examiner*—Deborah D. Carr

[57] ABSTRACT

The invention deals with the preparation, compositions, and application of certain high molecular weight polyesters of 12 hydroxystearic acid, which are useful in polycarbonate processing.

4 Claims, No Drawings

HYDROXYSTEARIC POLYESTERS OF GUERBET ALCOHOLS AS POLYCARBONATE LUBRICANTS

BACKGROUND OF THE INVENTION

1. Field of the Invention

The present invention deals with the preparation, compositions, and application of certain high molecular weight hydrophobic hydroxystearic polyesters which are useful in polycarbonate processing.

2. Description of the Art Practices

It is known that esters of simple alcohols may be used for various purposes including polycarbonate processing. In U.S. Pat. No. 3,784,595 issued Jan. 8, 1974 to Schirmer et al polycarbonate molding compositions are shown which are based on the esters of a trihydric alcohol and a saturated aliphatic carboxylic acid. U.S. Pat. No. 4,065,436 issued to Adelmann in Dec. 1977 describes thermoplastic molding compositions containing a mold release agent which is an ester of a saturated aliphatic carboxylic acid having from 10 to 20 carbon atoms per molecule and an aromatic hydroxy compound containing from 1 to 6 hydroxyl groups.

It is also known from U.S. Pat. No. 4,097,435 issued June 27, 1978 to Rawling et al that montanic acid ester waxes may be employed in polycarbonate molding compositions. U.S. Pat. No. 4,131,575 issued Dec. 26, 1978 to Adelmann describes in combination with aromatic polycarbonates, mold release agents which are the esters of saturated aliphatic carboxylic acids with alcohol containing from 4 to 6 hydroxyl groups. The disclosures of U.S. Pat. No. 4,131,575 are also found in the related British Patent No. 1,490,467 published Nov. 2, 1977. U.S. Pat. No. 4,143,024 issued Mar. 6, 1979 to Adelmann et al describes aromatic polycarbonate based thermoplastic molding compositions utilizing as a mold release agent the ester of a saturated aliphatic carboxylic acid containing from 10 to 20 carbon atoms per molecule and an aromatic hydroxyl compound from having 1 to 6 hydroxyl groups.

Lindner et al, U.S. Pat. No. 4,425,458, issued Jan. 10, 1984, teaches that specific guerbet alcohol diesters containing from 16 to 40 carbon atoms total in the guerbet alcohol molecule can be used as mold release agents in polycarbonate products.

U.S. Pat. No. 4,767,815 issued Aug. 30, 1988 to O'-Lenick teaches that two mole equivalents of a guerbet alcohol can be reacted with butryolactone to form a ether ester which can be used as a polycarbonate lubricant.

General disclosures of polycarbonate technology are found in U.S. Pat. No. 4,081,495 issued Mar. 28, 1978 to Freitag et al. Similar general disclosures are also found in U.S. Pat. No. 4,007,150 issued to Adelmann et al on Feb. 8, 1977.

To the extent that each of the foregoing patents is relevant to the present invention they are herein specifically incorporated by reference. Throughout the specification and claims, percentages and ratios are by weight, pressures are gauge and temperatures are Celsius unless otherwise noted.

SUMMARY OF THE INVENTION

The present invention is directed to a series of high molecular weight highly branched hydroxystearic polyesters, useful as a mold release agent for polycarbonate resin compositions. The polyesters are made in two sequential steps, first the condensation product of a 12-hydroxystearic acid with guerbet alcohols to make an ester having free hydroxyl and then subsequently reacted those groups with the equivalent amount of a suitable difunctional fatty acid preferably 12-hydroxystearic acid and capped with a fatty alcohol to make a polyester with little or no free hydroxyl and acid value.

Another aspect of the invention is a process used to prepare of these esters. Still another aspect of the invention is the process for the use of these novel products in polycarbonate and other thermoplastic molding processes.

DETAILED DESCRIPTION OF THE INVENTION

The present invention describes polyesters of 12-hydroxystearic acid. The polymeric structure is based upon the self polymerization of the difunctional hydroxy containing carboxylic acid such as 12-hydroxystearic acid. The compounds of the present invention are particularly functional in that polycarbonate resins, which have a high requirement for clarity since they are often used to form clear articles including safety glasses.

Unfortunately, the unlubricated polycarbonate resins tend to fail to release when molded, therefore agents must be employed to assist in releasing the polycarbonate resin from the mold. A substantial difficulty which has been found in the art is to ensure that the polycarbonate resin is not adversely affected by the mold release agent.

The molecules of this invention conform to the following generic structure;

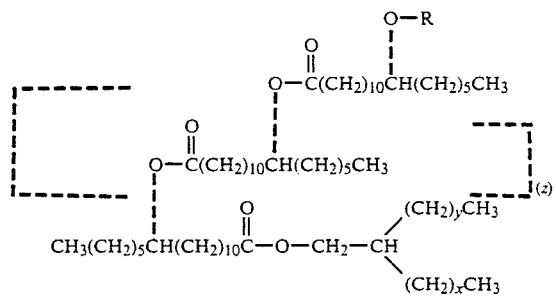

Wherein;

x and y are independently integers from 2 to 33;
z is an integer ranging from 1 to 200;
R is selected from H, or —C(O)R'
R' is alkyl or aryl having from C1H3 to C40H82.

In a preferred range x is an integer from 7 to 12; y is an integer from 7 to 12; z=1 to 20; R' is C11H22.

Guerbet Alcohols have been known since the 1890's when Marcel Guerbet first synthesized these materials (M. Guerbet, C.R. Acad. Sci. Paris, 128, 511; 1002 (1899)). These materials are high in molecular weight and are liquid even at very low temperatures.

The guerbet alcohols used in the present invention contain from about 12 to 40 carbon atoms (total) in the guerbet alcohol molecule. Preferably, the total number of carbon atoms in the guerbet alcohol molecule will be from about 20 to 36 carbon atoms and in particular 20 carbon atoms in each guerbet alcohol.

It is known in the art that guerbet alcohols may be formed from the same or different alcohols i.e. a homo or hetero system. That is, a guerbet alcohol is the condensation product of two alcohol molecules joined at the beta carbon of the alcohol which has retained the hydroxyl functionality. The resultant product is therefore a highly branched primary alcohol containing a single hydroxyl group. It is possible to obtain mixtures of alcohols and to condense them into hetero systems. It is also possible to obtain products which are guerbet alcohols from a short chained alcohol. It is desired for reasons of polarity, compatibility with and solubility in the polycarbonate system that homo-guerbet alcohols having between 16 and 40 carbon atoms be used.

It will be observed in the present invention that the mold release agents of this invention result in polycarbonate products in which neither the clarity nor the structural integrigity is not adversely affected. The polyesters of the present invention are observed to migrate sufficiently from the polycarbonate resin to the surface of the mold to effect release. Additionally, these esters do not substantially sweat out or collect on the surface of the molded articles. Sweating out cause hazing which is a disadvantage for most mold release agents. Another important aspect in working with mold release agents is the volatility of the compounds. It will of course be observed that the molding process requires large amounts of heat to liquefy the polycarbonate. This turn requires low volatility of the mold release agent so that the mold release agent is not lost to the atmosphere before it can function. It is also noted that an air pollution problem within a plant may arise where a mold release agent of high volatility is utilized. The products of the present invention will be observed to have low volatility thus presenting a distinct advantage over low molecular weight materials.

The polycarbonates with which the present polyesters are effective mold release agents include homopolycarbonates and copolycarbonates which are based, for example, on one or more of the following bisphenols: hydroquinone, resorcinol, dihydroxydiphenyls, bis-(hydroxyphenyl)-alkanes, bis-(hydroxyphenyl)-cycloalkanes, bis-(hydroxylphenyl)-sulphides, bis-(hydroxyphenyl)-ethers, bis-(hydroxylphenyl)-ketones, bis-(hydroxyphenyl)-sulphoxides, bis-(hydroxyphenyl)-sulphones and alpha, alpha-bis(hydroxyphenyl)-diisopropyl-benzenes, as well as their nuclear alkylated and nuclear-halogenated compounds. These are further suitable aromatic dihydroxy compounds are described, for example, in U.S. Pat. Nos. 3,028,365, 2,999,835, 3,148,172, 3,271,368, 2,991,273, 3,271,367, 3,280,078, 3,014,891 and 2,999,846, in German Offenlegungsschriften (German Published Specifications) Nos. 1,570,703, 2,063,050, 2,063,052, 2,211,956, and 2,211,957, in French Patent Specification No. 1,561,518 and in the monograph "H. Schnell, Chemistry and Physics of Polycarbonates, Interscience Publishers, New York, 1964".

Preferred bisphenols are those of the formula I shown below:

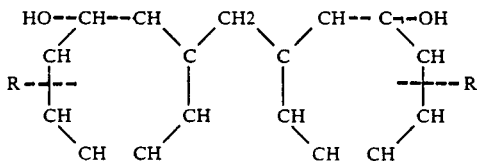

in which R is identical or different and denotes H, C1-alkyl, Cl or Br, and in which X is a bond, C1C8-alkylene, C2-alkylidene, C5-C15cycloalkylene, C5-C15-cycloalkylidene, —SO— or formula II shown below:

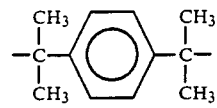

Examples of these bisphenols are
4,4'-dihydroxydiphenyl,
2,2-bis-(4-hydroxyphenyl)-propane,
2,4-bis(4-hydroxyphenyl)-2-methylbutane,
1,1-bis-(4-hydroxyphenyl)-cyclohexane,
a,a-bis(4-hydroxyphenyl)-p-diisopropylbenzene,
2,2-bis-(3-methyl-4-hydroxyphenyl)-propane,
2,2-bis-(3-chloro-4-hydroxyphenyl)-propane,
bis-(3,5-dimethyl-4-hydroxyphenyl)-propane,
bis(3,5)-dimethyl-4-hydroxyphenyl)-2-methylbutane,
1,1-bis-(3,5-dimethyl-4-hydroxyphenyl)-cyclohexane,
a,a-bis-(3,5-dimethyl-4-hydroxyphenyl)-p-diisopropylbenzene,
2,2-bis-(3,5-dichloro-4-hydroxyphenyl)-propane and
2,2-bis(3,5-dibromo-4-hydroxyphyenyl)-propane.

Examples of particularly preferred bisphenols are:
2,2-bis-(4-hydroxyphenyl)-propane,
2,2-bis(3,5-dimethyl-4-hydroxyphenyl)-propane,
2,2-bis-(3,5-dichloro-4-hydroxyphenyl)-propane,
2,2-bis-(3,5-dibromo-4-hydroxyphenyl)-propane, and
1,1-bis-(4-hydroxyphenyl)-cyclohexane.

Preferred aromatic polycarbonates are those which are based on one or more of the bisphenols mentioned as being preferred. Particularly preferred copolycarbonates are those based on 2,2-bis-(4-hydroxyphenyl)-propane and one of the other bisphenols mentioned as being particularly preferred. Further particularly preferred polycarbonates are those based solely on 2,2-bis-(4-hydroxyphenyl)-propane or 2,2-bis-(3,5-dimethyl-4-hydroxyphenyl)-propane.

The aromatic polycarbonates can be prepared in accordance with know processes, such as, for example, in accordance with the melt trans-esterification process from bisphenols and diphenyl carbonate and the two-phase boundary process from bisphenols and phosgene, as described in the above mentioned literature.

The aromatic high-molecular weight polycarbonates can be branched due to the incorporation of small amounts, preferably of between 0.05 and 2.0 mol % (relative to diphenols employed), of trifunctional or more than trifunctional compounds, especially compounds with three of more phenolic hydroxyl groups.

Polycarbonates of this type are described, for example, in German Offenlegungsschriften (German Published Specifications) Nos. 1,570,533, 1,595,762, 2,116,974 and 2,113,347; British Patent Specification No. 1,079,821; U.S. Pat. No. 3,544,514 and German Patent Application No. P25 00 092.4.

Some examples of compounds with three or more than three phenolic hydroxyl groups which can be used are phloroglucinol, 4,6-dimethyl-2,4,6-tri-(4-hydroxyphenyl)-heptane-2,4,6-dimethyl-2,4,6-tri-(4-hydroxyphenyl)-heptane, 1,4,5-tri-(4-hydroxyphenyl)-benzene, 1,1,1-tri-(4-hydroxphenyl)-ethane, tri-(4-hydroxyphenyl)-phenylmethane, 2,2-bis-(4,4-bis-(4-hydroxyphenyl)-cyclohexyl)-propane, 2,4-bis-(4-hydroxyphenylisopropyl)-Phenol, 2,6-bis-(2-hydrox-5-methyl-benzyl)-4-methylphenol, 2-(4-hydroxyphenyl), 2-2,4-dihydroxyphenyl)-propane, hexa(4-(4-hydroxyphenylisopropyl)phenyl)orthoterephthalic acid ester, tetra-(4-hydroxyphenyl)-methane and 1,4-bis-((4',4"- dihydroxytriphenyl)methyl)-benzene. Some of the other trifunctional compounds are 2,4-dihydroxybenzoic acid, trimesic acid, cyanuric chloride and 3,3-bis-(4-hydroxyphyenyl)-2-oxo-2,3-dihydroindole.

The aromatic high-molecular polycarbonates should as a rule have mean weight-average molecular weights M of at least 10,000; especially of 10,000 to 200,000; preferably of 20,000 to 80000; determined by measuring the relative viscosity in CH2Cl2 at 25 degrees c. and a concentration of 0.5% by weight.

The thermoplastic polycarbonate molding compositions find use in several areas. Such examples of use for the polycarbonates of the present invention utilizing the mold release agents include the electrical industry and the optical field such as the stripping of sockets, coiled bodies, complicated housings, projector housings, switch cabinet bottoms, medical plastics and other similar applications.

The mold release agent of the present invention is utilized with the polycarbonate in the manner of similar prior polycarbonate formulations. The level of use of the ester to the polycarbonate is from about 0.0025% to about 10.0%; preferably from about 0.1% to about 0.25% by weight of the total polycarbonate compositions.

The compounds of this invention are prepared by condensing 12-hydroxystearic acid with a guerbet alcohol to make an ester compound which is subsequently reacted with additional 12-hydroxystearic acid the subsequently reacted with a fatty acid to reduce the acid value and hydroxyl value to vanishingly low levels. The presence of the acid value and the hydroxyl value is detrimental to the functional attributed of the lubricant. Most importantly, clarity and dimensional stability are affected.

EXAMPLES

The Guerbet alcohols used as raw materials are items of commerce and are prepared by processes known to those skilled in the art. They are produced by several manufacturers including; Exxon Chemicals Corporation (Darien Ct.) and Henkel Corporation (Ambler Pa).

Reaction Conditions

The esterification can be run without catalyst; however, when no catalysts are used reaction rates are inefficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titanates, organo tin compounds, organo zinc compounds, zinc oxide, magnesium oxide, calcium oxide, etc. Preferred is stannous oxylate. The reaction is conducted at between 140 and 240 C. under an inert nitrogen blanket. Preferred temperature range is between 180 and 210 C. Water is removed from the reaction which is done using a nitrogen sparge or vacuum of up to 10 mm.

The following are suggested embodiments of present invention.

EXAMPLE 1

To a suitable reaction vessel is added 150 grams of 12-hydroxystearic acid, 2.0 grams of stannous oxylate catalyst and 150 grams of a C20 guerbet alcohol. A nitrogen sparge is then applied. Next the temperature is increased to 160-200 C. and by-product water begins to distill off. Vacuum is applied to keep the water distilling. When 97% of the theoretical water is removed the reaction is cooled. The desired product is obtained without and additional purification.

EXAMPLE 2

To a suitable reaction vessel is added 300 grams of the ester from Example 1 with 2.0 grams of sulfuric acid and 1080 grams of 12-hydroxystearic acid. A nitrogen sparge is then applied. Next the temperature is increased to 160-200 C. and by-product water begins to distill off. Vacuum is applied to keep the water distilling. When 97% of the theoretical water is removed the reaction is cooled. The desired product is obtained without and additional purification.

EXAMPLE 3

To a suitable reaction vessel is added 1290 grams of the ester from Example 2 with 2.0 grams of sulfuric acid and 93 grams of dodecanoic acid. A nitrogen sparge is then applied. Next the temperature is increased to 160-200 C. and by-product water begins to distill off. Vacuum is applied to keep the water distilling. When 97% of the theoretical water is removed the reaction is cooled. The desired product is obtained without and additional purification.

EXAMPLE 4

To a suitable reaction vessel is added 3000 grams of 12-Hydroxy Stearic Acid, 10.0 grams of stannous oxylate catalyst and 2430 grams of C16 guerbet alcohol. A nitrogen sparge is then applied. Next the temperature is increased to 160-200 C. and by-product water begins to distill off. Vacuum is applied to keep the water distilling. When 97% of the theoretical water is removed the reaction is cooled. The desired product is obtained without and additional purification.

EXAMPLE 5

To a suitable reaction vessel is added 5440 grams of ester from Example 4, 82.0 grams of p-toluene sulfonic acid catalyst and 36,000 grams of 12-hydroxystearic acid. A nitrogen sparge is then applied. Next the temperature is increased to 160-200 C. and by-product water begins to distill off. Vacuum is applied to keep the water distilling. When 97% of the theoretical water is removed the reaction is cooled. The desired product is obtained without and additional purification.

EXAMPLE 6

To a suitable reaction vessel is added 4000 grams of the ester from Example 5 with 8.0 grams of sulfuric acid and 46 grams of formic acid. A nitrogen sparge is then applied. Next the temperature is increased to 160-200 C. and by-product water begins to distill off. Vacuum is applied to keep the water distilling. When 97% of the theoretical water is removed the reaction is cooled. The desired product is obtained without and additional purification.

EXAMPLE 7

To a suitable reaction vessel is added 3000 grams of 12-Hydroxy Stearic Acid, 13.0 grams of magnesium oxide catalyst and 3550 grams of C24 guerbet alcohol. A nitrogen sparge is then applied. Next the temperature is increased to 160-200 C. and by-product water begins to distill off. Vacuum is applied to keep the water distilling. When 97% of the theoretical water is removed the reaction is cooled. The desired product is obtained without and additional purification.

EXAMPLE 8

To a suitable reaction vessel is added 6380 grams of ester from Example 7, 25.0 grams of p-toluene sulfonic acid catalyst and 6000 grams of 12-hydroxystearic acid. A nitrogen sparge is then applied. Next the temperature is increased to 160-200 C. and by-product water begins to distill off. Vacuum is applied to keep the water distilling. When 97% of the theoretical water is removed the reaction is cooled. The desired product is obtained without and additional purification.

EXAMPLE 9

To a suitable reaction vessel is added 1204 grams of the ester from Example 8 with 3 grams of sulfuric acid and 282 grams of stearic acid. A nitrogen sparge is then applied. Next the temperature is increased to 160-200 C. and by-product water begins to distill off. Vacuum is applied to keep the water distilling. When 97% of the theoretical water is removed the reaction is cooled. The desired product is obtained without and additional purification.

EXAMPLE 10

To a suitable reaction vessel is added 3000 grams of 12-Hydroxy Stearic Acid, 14.0 grams of magnesium oxide catalyst and 4320 grams of C36 guerbet alcohol. A nitrogen sparge is then applied. Next the temperature is increased to 160-200 C. and by-product water begins to distill off. Vacuum is applied to keep the water distilling. When 97% of the theoretical water is removed the reaction is cooled. The desired product is obtained without and additional purification.

EXAMPLE 11

To a suitable reaction vessel is added 7150 grams of ester from Example 10, 44.0 grams of p-toluene sulfonic acid catalyst and 15000 grams of 12-hydroxystearic acid. A nitrogen sparge is then applied. Next the temperature is increased to 160-200 C. and by-product water begins to distill off. Vacuum is applied to keep the water distilling. When 97% of the theoretical water is removed the reaction is cooled. The desired product is obtained without and additional purification.

EXAMPLE 12

To a suitable reaction vessel is added 21,290 grams of the ester from Example 11 with 46 grams of sulfuric acid and 1720 grams of decanoic acid. A nitrogen sparge is then applied. Next the temperature is increased to 160-200 C. and by-product water begins to distill off. Vacuum is applied to keep the water distilling. When 97% of the theoretical water is removed the reaction is cooled. The desired product is obtained without and additional purification.

| Example | Moles 12HSA | Legend Guerbet Type/ Moles | Moles 12HSA | R' |
|---|---|---|---|---|
| 1 | 1 | C20/1 | — | — |
| 2 | | Example 1 | 7 | — |
| 3 | | Example 2 | | C11H24 |
| 4 | 1 | C16/1 | — | — |
| 5 | | Example 4 | 12 | — |
| 6 | | Example 5 | | CH3 |
| 7 | 1 | C24/1 | — | — |
| 8 | | Example 7 | 2 | — |
| 9 | | Example 8 | | C17H38 |
| 10 | 1 | C36/1 | — | — |
| 11 | | Example 10 | 2 | — |
| 12 | | Example 11 | | C9H20 |

What is claimed is:

1. A compound conforming to the following structure;

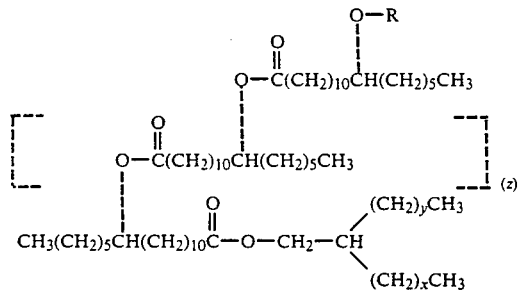

Wherein;
x and y are independently integers from 2 to 33;
z is an integer ranging from 1 to 200;
R is selected from H, or —C(O)R';
R' is alkyl or aryl having from C1H3 to C40H82.
2. The compound of claim 1 wherein z is 5.
3. The compound of claim 1 wherein R is H.
4. The compound of claim 1 wherein x is 7, y is 9, z is 4.5 and R' is C9H20.

* * * * *